US006489305B1

(12) United States Patent
Demers

(10) Patent No.: US 6,489,305 B1
(45) Date of Patent: Dec. 3, 2002

(54) METHODS AND COMPOSITIONS FOR THE TREATMENT OF OCULAR DISEASES

(75) Inventor: G. William Demers, San Diego, CA (US)

(73) Assignee: Canji, Inc., San Diego, CA (US)

(*) Notice: Subject to any disclaimer, the term of this patent is extended or adjusted under 35 U.S.C. 154(b) by 0 days.

(21) Appl. No.: 09/075,505

(22) Filed: May 8, 1998

(51) Int. Cl.[7] ............................................. A61K 48/00
(52) U.S. Cl. ...................... 514/44; 424/93.2; 435/320.1
(58) Field of Search .............................. 424/93.1, 93.2, 424/93.21, 427, 422, 450, 451; 435/320.1; 514/44

(56) References Cited

U.S. PATENT DOCUMENTS

| | | | |
|---|---|---|---|
| 5,302,706 A | 4/1994 | Smith et al. ................ | 536/23.1 |
| 5,621,082 A | 4/1997 | Xiong et al. ................ | 530/350 |
| 5,624,819 A | 4/1997 | Skolnick et al. ............ | 435/69.1 |
| 5,756,283 A | * 5/1998 | Wilson et al. ................. | 435/5 |
| 5,827,702 A | 10/1998 | Cuthbertson ............. | 435/172.1 |
| 6,027,742 A | * 2/2000 | Lee et al. .................... | 424/422 |
| 6,218,372 B1 | * 4/2001 | Nabel et al. .................. | 514/44 |
| 6,242,201 B1 | * 6/2001 | Lane et al. ................. | 435/7.23 |
| 6,274,614 B1 | * 8/2001 | Richter et al. ............. | 514/410 |

FOREIGN PATENT DOCUMENTS

| | | |
|---|---|---|
| AU | B-61444/94 | 9/1994 |
| WO | WO 9409135 A1 | 4/1994 |
| WO | WO 9528483 A1 | 10/1995 |
| WO | 96/14334 | * 5/1996 |
| WO | WO 9619244 A1 | 6/1996 |
| WO | WO 9635704 A1 | 11/1996 |
| WO | WO 9703635 A2 | 2/1997 |
| WO | WO 9711174 A1 | 3/1997 |
| WO | WO 97/37542 | 10/1997 |

OTHER PUBLICATIONS

US 5,691,198, 11/1997, Jin et al. (withdrawn)
A. Divan, et al., "p53 Expression Correlates with Apoptosis but not with p21, waf Expression in Retinoblastomas"; *Journal of Pathology* (1997), vol. 182, pp. 6A.
A.F. Wright, "Gene therapy for the eye"; *Br.J. Ophthalmol* (Aug. 1, 1997), 81: pp. 620–623.
C.A. Schubert, et al. "Retrovirus–mediated transfer of the suicide gene into retinal pigment epithelial cells in vitro"; *Curr. Eye Res.* (Jul. 1, 1997), 16: pp. 656–662.
L. da Cruz, et al., "Ocular gene therapy: The basic science and current state of research"; *Aust N.Z. J. Ophthalmol.* (May 1, 1997), 25: pp. 97–104.
H.J. Xu, "Strategies for Approaching Retinoblastoma Tumor Suppressor Gene Therapy"; *Adv. Pharmacol.* (Jan. 1, 1997), 40: pp. 369–397.
N.G. Della, "Molecular Biology in Ophthalmology. A Review of Principles and Recent Advances." *Arch. Opthalmol.* (Apr. 1, 1996), 114: 457–463.

R.B. Nussenblatt, et al., "Perspectives on Gene Therapy in the Treatment of Ocular Inflammation."; *Eye* (1997), 11: pp. 217–221.
D. Stephan, et al., "Gene and other biological therapies for vascular diseases."; *Fundam Clin. Pharmacol.* (Jan. 1997), 11: pp. 97–110.
J.A. Eastham, et al., "In vivo gene therapy with p53 or p21 Adenovirus for Prostate Cancer."; *Cancer Res.* (Nov. 15, 1995), 55: pp. 5151–5155.
D.T. Denhardt, "Oncogene–Initiated Aberrant Signaling Engenders the Metastatic Phenotype: Synergistic Transcription Factor Interactions are Targets for Cancer Therapy."; *Crit. Rev. Oncog.* (1996), 7(3–4): 261–291.
A.L. Gartel, et al., "p21—Negative Regulator of the Cell Cycle."; *Proc. Soc. Exp. Biol. Med.* (Nov. 1996), 213: pp. 138–149.
S.D. Morgenbesser, et al., "p53–dependent apoptosis produced by Rb–deficiency in the developing mouse lens."; *Nature* (Sep. 1, 1994), 371(6492): 72–74.
David A. Alcorta, "Involvement of the cyclin–dependent kinase inhibitor p16 (INK4a) in replicative senescence of normal human fibroblasts."; *Proc. Natl. Acad. Sci.* (1996), 93: pp. 13742–13747.
Elisa A. Spillare, "Suppression of Growth in Vitro and Tumorigenicity in Vivo of Human Carcinoma Cell Lines by Transfected p16$^{INK4}$"; *Mol. Carcinog.* (1996), 16: 53–60.
Corinne Cayrol, et al., "p21 binding to PCNA causes G1 and G2 cell cycle arrest in p53–deficient cells"; *Oncogene* (1998), 16: 311–320.
Joseph A. Erhardt, et al., "p21$^{WAF1}$ induces permanent growth arrest and enhances differentiation, but does not alter apoptosis in PC12 cells."; *Oncogene* (1998) 16: 443–451.
René H. Medema, et al., "p21$^{waf1}$ can block cells at two points in the cell cycle, but does not interfere with processive DNA–replication or stress–activated kinases"; *Oncogene* (1998) 16: 431–441.
Ali et al., *Hum. Mol. Genet.* (1996) 5: 591–594.
Arteaga et al., *Cancer Research* (1996) 56(5): 1098–1103.
Bennett et al., *Hum. Gene Ther.* (1996) 7: 1763–1769.
Cayouette and Gravel, *Hum. Gen Ther.* (1997) 8: 423–430.
Chang et al., *J. Clin. Invest.* (1995) 96: 2260–2268.
Dalesandro et al., *J. Thorac. Cardi Surg.* (1996) 111(2): 416–422.
Dunaief et al., *Hum. Gene Ther.* (1995) 6: 1225–1229.
Fromm et al., *Dev. Genet.* (1997) 20: 276–287.
Hermens et al., *J. Neurosci. Methods* (1997) 71: 85–98.
Koc et al., *Seminars in Oncology* (1996) 23(1): 46–65.
Li et al.,*Proc. Natl. Acad. Sci. U.S.A.* (1995) 92: 7700–7704.
Makarov et al., *Proc. Natl. Acad. Sci. U.S.A.* (1996) 93(1): 402–406.
Mashhour, *Gene Ther.* (1994) 1:122–126.

(List continued on next page.)

Primary Examiner—Dave T. Nguyen
(74) Attorney, Agent, or Firm—Townsend and Townsend and Crew LLP

(57) ABSTRACT

Methods and composition for the treatment of ocular disease with a cyclin dependent kinase inhibitor are provided.

25 Claims, 2 Drawing Sheets

OTHER PUBLICATIONS

Murata et al, *Ophthalmic Res.* (1997) 29: 242–251.
Nolta et al., *Proc. Natl. Acad. Sci. U.S.A.* (1996) 93(6): 2414–2419.
Okamoto et al., *Proc. Natl. Acad. Sci. U.S.A.* (1994) 91(23): 11045–11049.
Raper et al., *Annals of Surgery* (1996) 223(2): 116–126.
Sakamoto et al., *Ophthalmology* (1995) 102: 1417–1424.
Bridge et al. Journal of Virology. 63(2): 631–8, Feb. 1989.*
Ledley, FD. Pharmaceutical Research. 13: 1595–1613, Nov. 1996.*
Jomary et al. FEBS Letters. 347: 117–122, 1994.*
Sakamoto et al. Gene Therapy. 5: 1088–1097, May 1998.*
Rakoczy et al. Drug Development Research. 46: 277–285, 1999.*
Ratiglia et al. IOVS, 39(4): S724, Mar. 1998.*
Ueno et al. Annals of the NY Academy of Sciences. 811: 401–411, Apr. 1997.*
Alcorta et al. Proc Natl Acad Sci. 93: 13742–13747, Nov. 1996.*
Afshari et al. Cell Growth Differ. 7(8): 979–988, Aug. 1996.*

* cited by examiner

METHODS AND COMPOSITIONS FOR THE TREATMENT OF OCULAR DISEASES

BACKGROUND OF THE INVENTION

Gene therapy has been proposed as an approach to the treatment of ocular diseases by a number of investigators. Hermens et al. (*J. Neurosci. Methods* 71:85–98 (1997)) disclosed the injection of an adenoviral vector containing a lacZ gene as a reporter gene into the central and peripheral nervous system of the rat. In that system areas with a laminar structure such as the eye demonstrated more widespread transgene expression. Ali et al. (*Hum. Mol. Genet.* 5:591–5949 (1996)) disclosed the use of an adeno-associated virus (AAV) as a vector carrying lacZ to transduce all layers of the neuroretina as well as the retinal epithelium following subretinal injection. Mashhour (*Gene Ther.* 1:122–126 (1994)) disclosed that injection of an adenovirus vector carrying lacZ into the vitreous body, the anterior chamber, or the peribulbar body of mice did not result in any detectable cytopathic effect and was associated with endocytosis of viral particles in corneal, photoreceptor, bipolar, ganglionic, and oculomotor muscle cells, depending on the administration route.

The use of gene therapy to treat heritable diseases of the eye in particular has been proposed by several researchers. For example, Li et al. (*Proc. Natl. Acad. Sci. U.S.A.* 92:7700–7704 (1995)) disclosed the use of adenovirus-mediated transfer of human beta-glucuronidase cDNA expressed under the control of a non-tissue specific promoter injected intravitreally or subretinally to reverse the pathological changes of lysosomal storage disease in the eyes of mice with mucopolysaccharidosis VII.

Rescue of photoreceptors by gene therapy has been demonstrated in several experimental systems. Cayouette and Gravel (*Hum. Gene Ther.* 8:423–430 (1997)) disclosed adenovirus-mediated gene transfer of ciliary neurotropic factor prevented photoreceptor degeneration in the retinal degeneration (rd) mouse, an animal model of retinitis. pigmentosa Bennett et al. (*Hum. Gene Ther.* 7:1763–1769 (1996)) disclosed the rescue of photoreceptor cells in rd mice using a recombinant replication defective adenovirus containing murine cDNA for beta phosphodiesterase. Dunaeif et al. (*Hum. Gene Ther.* 6:1225–1229 (1995)) disclosed retroviral gene transfer into retinal pigment epithelial cells followed by transplantation into rat retina in an experimental rat model to preserve photoreceptors.

The use of suicide genes delivered by recombinant viral vectors to kill ocular cells has focused mainly on the use of the herpes thymidine kinase gene. For example, Sakamoto, et al. (*Ophthalmology* 102:1417–1424 (1995) described the inhibition of experimental proliferative vitreoretinopathy by retroviral vector-mediated transfer of the herpes simplex thymidine kinase gene. Murata et al. (*Ophthalmic Res.* 29:242–251 (1997) described the use of retroviral vectors to transfer the herpes simplex virus thymidine kinase gene in a rabbit model of proliferative vitreoretinopathy.

The role of tumor suppressor genes such as p16, p21, p53, or RB in hyperproliferative diseases of the eye has been challenging to elucidate. Studies of cell cycle regulation in the ocular lens using transgenic mice have shown that inactivation of RB can cause postmitotic lens fiber cells to enter the cell cycle. However, when p53 is present, inactivation of RB in this cell type results in cell death rather than continued proliferation. Although p53 is known to upregulate expression of the cyclin-dependent kinase inhibitor p21, overexpression of p21 in transgenic lens is not sufficient to cause apoptosis in transgenic mouse lens (Fromm et al. *Dev. Genet.* 20:276–287 (1997)). In vascular tissue, Chang et al. (*J. Clin. Invest.* 96:2260–2268 (1995)) discloses that adenovirus mediated overexpression of p21 inhibits vascular smooth muscle cell (VSMC) proliferation in vitro by arresting VSMCs in the G1 phase of the cell cycle. In addition, Chang, et al. demonstrated that localized adenoviral delivery of p21 in conjunction with balloon angioplasty significantly reduced neointima hyperplasia in the rat carotid artery model of restenosis.

SUMMARY OF THE INVENTION

The present invention discloses methods and compositions for the treatment of ocular diseases. In particular, the present invention provides a method for the treatment of ocular hyperproliferative diseases by the administration of cyclin dependent kinase inhibitors. The present invention further provides pharmaceutical formulations for the intracellular delivery of cyclin dependent kinase inhibitors.

BRIEF DESCRIPTION OF THE DRAWINGS

FIG. 1 comprises FIGS. 1A and 1B, which depict the response of ocular fibroblasts to infection with recombinant adenoviruses as described in Example 3 herein.

DESCRIPTION OF THE PREFERRED EMBODIMENT

Figure 1A:
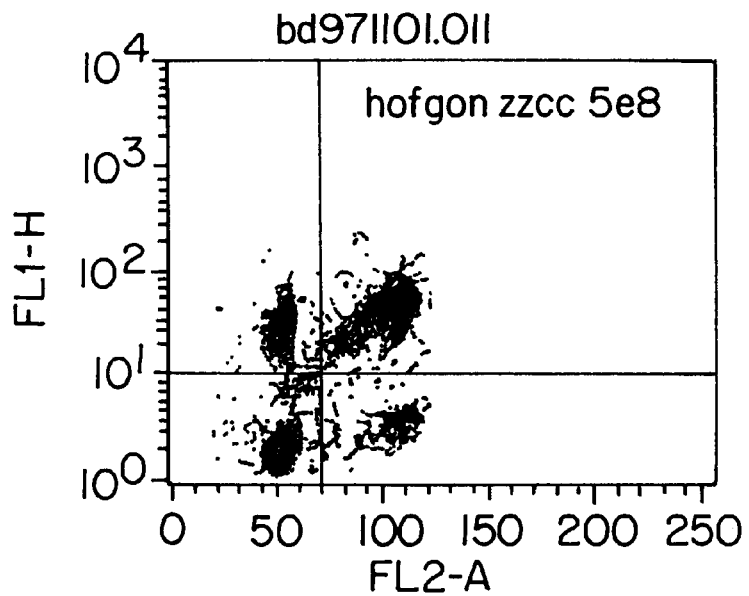
FIG. 1A indicates the response of hofgon cells to a dose of $5 \times 10^8$ TOCC viral particles (rAd-p21).

All publications and patent applications cited in this specification are herein incorporated by reference in their entirety for all purposes as if each individual publication or patent application were specifically and individually indicated to be incorporated by reference.

The present invention provides a method of treating ocular disease by the administration of cyclin dependent kinase inhibitors. Cyclin dependent kinase inhibitors may be administered as proteins or by the administration of a recombinant vector containing the cyclin dependent kinase inhibitor coding sequence permitting intracellular expression of the cyclin dependent kinase inhibitor coding sequence in the target cell. The present invention further provides pharmaceutical formulations of cyclin dependent kinase inhibitors and vectors containing the coding sequences for cyclin dependent kinase inhibitors. Particularly preferred cyclin dependent kinase inhibitors are p16 and p21. Particularly preferred vectors include recombinant adenoviral vectors, plasmid vectors, retroviral and herpes viral vectors.

The present invention demonstrates that the administration of pharmaceutical formulations comprising cyclin dependent kinase inhibitors are particularly effective in the treatment of diseases of the eye associated with hyperproliferation where other hyperproliferative agents, such as pRB56, are ineffective. The present invention demonstrates the utility of cyclin dependent kinase inhibitors, such as p21 and/or p16, are useful in the treatment of ocular diseases, especially those associated with hyperproliferation of fibroblasts and retinal pigmented epithelial cells, as well as angiogenic diseases associated with the proliferation of endothelial cells.

A. Preclinical Model

In the practice of the invention as exemplified herein, recombinant adenoviral vectors encoding p16 (XTCC), p21 (TOCC) and p56RB (QLCC) and a null control vector (ZZCC) prepared in substantial accordance with the teaching of Example 1 below. As a preclinical model of the treatment of ocular hyperproliferative disease, three human ocular fibroblast (HOF) cell lines obtained from different human donors were prepared and infected with the recombinant adenoviral constructs in substantial accordance with the teaching of Examples 2, 3 and 4 herein. The percentage of cellular proliferation was determined by FACS analysis. As can be seen from the data presented in Table 1 below, in each case the vector containing the p21 or p16 transgene (TOCC or XTCC respectively) was more effective than control vector (ZZCC) or the vector containing the p56 RB transgene (QLCC) as measured by BrdU labeling. A dose dependent inhibition of BrdU incorporation was detected in each case. This was not limited to the kinase inhibitor rAd-constructs, as the null control and RB56 rAd-constructs also inhibited BrdU incorporation in a dose dependent manner.

TABLE 1

Inhibition of Human Ocular Fibroblasts

| Cell Line | Vector | dose | G1 (%) | S (%) | G2 (%) |
| --- | --- | --- | --- | --- | --- |
| HOF-GON | ZZCC | $5 \times 10^8$ | 49 | 48 | 3 |
| HOF-GON | QLCC | $5 \times 10^8$ | 52 | 43 | 5 |
| HOF-GON | TOCC | $5 \times 10^8$ | 81 | 7 | 12 |
| HOF-GON | XTCC | $5 \times 10^8$ | 88 | 4 | 7 |
| HOF-GON | ZZCC | $5 \times 10^9$ | 67 | 3 | 0 |
| HOF-GON | QLCC | $5 \times 10^9$ | 79 | 13 | 7 |
| HOF-GON | TOCC | $5 \times 10^9$ | 91 | 0 | 9 |
| HOF-GON | XTCC | $5 \times 10^9$ | 90 | 0 | 10 |
| HOF-NEP | ZZCC | $5 \times 10^8$ | 19 | 76 | 5 |
| HOF-NEP | QLCC | $5 \times 10^8$ | 21 | 74 | 5 |
| HOF-NEP | TOCC | $5 \times 10^8$ | 47 | 37 | 16 |
| HOF-NEP | ZZCC | $5 \times 10^9$ | 52 | 36 | 12 |
| HOF-NEP | QLCC | $5 \times 10^9$ | 61 | 26 | 13 |
| HOF-NEP | TOCC | $5 \times 10^9$ | 81 | 0 | 19 |
| HOF-SCH | ZZCC | $5 \times 10^8$ | 40 | 53 | 6 |
| HOF-SCH | QLCC | $5 \times 10^8$ | 42 | 51 | 8 |
| HOF-SCH | XTCC | $5 \times 10^8$ | 83 | 5 | 12 |
| HOF-SCH | ZZCC | $5 \times 10^9$ | 78 | 8 | 15 |
| HOF-SCH | QLCC | $5 \times 10^9$ | 83 | 6 | 11 |
| HOF-SCH | XTCC | $5 \times 10^9$ | 88 | 0 | 11 |

These data were confirmed by a second method, $^3$H-thymidine incorporation to assess cell proliferation. In this assay a dose response was measured and compared to untreated control cells. These data supported the BrdU incorporation assay in that the p21 and p16 rAd constructs were able to inhibit $^3$H-thymidine incorporation at lower doses than the no transgene or RB56 rAd constructs. The estimated $ED_{50}$ was about 10 fold lower with the p16 and p21 vector constructs than rAd-null or rAd-RB56. Also similar to the observation in the BrdU incorporation assay, there was a dose-dependent inhibition of 3H-thymidine incorporation with the control rAd-null and rAd-RB56 constructs.

Additional experiments were performed comparing the activity of rAd-p56RB, rAd-p21, rAd-p16 and rAd-p53 in additional human ocular fibroblast cells. Treatment of fibroblasts with rAd expressing p21, p16, or p53 resulted in dramatically reduced percentage of cells incorporating BrdU and conversely retained a higher percentage of cells in G0/G1 phase. Based on the GFP analysis it can be estimated that at a dose of $1 \times 10^9$ PN/ml all of the cells were expressing the respective transgene. This was the second lot of TOCC to be tested and cells responded to this lot similarly as to the first lot. Cells treated with QLCC did not respond differently than cells treated with ZZCC. Cells derived from two different human donors gave comparable responses to each of the constructs. It is therefore expected that TOCB and other vector constructs expressing p21 will be effective at inhibition of S phase entry as demonstrated with TOCC.

TABLE 2

Cell cycle analysis of HOF cells treated with rAd and released from serum starvation.

| Vector | % g0/g1 | % s | % g2/m |
| --- | --- | --- | --- |
| HOFtol ut | 37 | 60 | 4 |
| HOFtol gfcb 1e8 | 39 | 57 | 4 |
| HOFtol ftcb 1e8 | 47 | 49 | 4 |
| HOFtol gfcb 1e9 | 50 | 45 | 5 |
| HOFtol ftcb 1e9 | 78 | 14 | 8 |
| HOFtol qlcc 1e8 | 38 | 57 | 4 |
| HOFtol tocc 1e8 | 65 | 27 | 8 |
| HOFtol xtcc 1e8 | 69 | 23 | 8 |
| HOFtol zzcc 1e8 | 43 | 52 | 5 |
| HOFtol qlcc 1e9 | 44 | 50 | 7 |
| HOFtol tocc 1e9 | 89 | 0 | 11 |
| HOFtol xtcc 1e9 | 91 | 2 | 8 |
| HOFtol zzcc 1e9 | 47 | 50 | 3 |
| HOFcar ut | 50 | 41 | 9 |
| HOFcar gfcb 1e8 | 52 | 41 | 7 |
| HOFcar ftcb 1e8 | 62 | 30 | 8 |
| HOFcar gfcb 1e9 | 68 | 25 | 7 |
| HOFcar ftcb 1e9 | 88 | 2 | 9 |
| HOFcar qlcc 1e8 | 50 | 41 | 8 |
| HOFcar tocc 1e8 | 82 | 9 | 10 |
| HOFcar xtcc 1e8 | 80 | 11 | 9 |
| HOFcar zzcc 1e8 | 62 | 31 | 6 |
| HOFcar qlcc 1e9 | 69 | 23 | 8 |
| HOFcar tocc 1e9 | 91 | 1 | 9 |
| HOFcar xtcc 1e9 | 89 | 1 | 10 |
| HOFcar zzcc 1e9 | 71 | 22 | 7 |

In summary, the treatment of these cells with QLCC (rAD-RB56) did not demonstrate an effect greater than the control vector, ZZCC. However, these data demonstrate that treatment of human ocular cells with genes expressing cyclin dependent kinase inhibitors such as p16 or p21 is an effective therapy for treatment of ocular diseases.

B. Cyclin Dependent Kinase Inhibitors

The term cyclin dependent kinase inhibitors includes the human, p27kip, p57kip2, p15ink4b, p18ink4c, p19ink4d, p16ink4a and p21sdi wild-type proteins, homologous protein sequences from other organisms, as well as any mutations or truncations thereof which display essentially the same function as the wild-type polynucleotide or protein sequence as well as polynucleotide sequences encoding same.

1. p16

The term "p16" is meant to refer to a 156 amino acid polypeptide having the amino acid sequence provided below: (SEQ ID NO: 3):

MEPAAGSSMEPSADWLATAAAR-
GRVEEVRALLEAGALPNAPNSYGRRPIQVM MMGSAR-
VAELLLLHGAEPNCADPATLTRPVH-
DAAREGFLDTLVVLHRAGARL
DVRDAWGRLPVDLAEELGHRDVARYL-
RAAAGGTRGSNHARIDAAEGPSDIPD

The p16 molecule has been referred to in the literature by the following names: CDKN2A, CDK4I, Hs.1174, MLM, p16, INK4, MTS1, CMM2, CDKN2 and cyclin-dependent kinase inhibitor 2A.

The human p16 genomic coding sequence is arranged in three exons on human chromosome 9p. The human cDNA coding sequence is well known in the literature (See Okamoto, A. et al., (1994) *Proc. Natl. Acad. Sci. U.S.A.* 91 (23), 11045–11049) and is available as GenBank Accession Number L272112.

2. p21

The wild type p21 protein is a 164 amino acid protein having cell regulatory functions. The cDNA and protein sequence are desribed in Smith, et al., U.S. Pat. No. 5,302, 706 issued Apr. 12, 1994, the entire teaching of which is herein incorporated by reference. p21 is also known in the scientific literature as p21sdi, p21wafl, p21cipl and p21picl. The term p21 also includes polynucleotide sequence encoding the human wild-type protein and homologous sequences from other organisms, as well as any mutations, truncations, or anti-sense nucleic acid which displays essentially the same function as the wild-type polynucleotide or protein sequence.

C. Delivery Systems

When the method of treatment to be employed is to introduce a nucleotide sequence encoding p16 or p21, it is possible to incorporate the naked plasmid into a cell However, when delivering the p16 or p21 coding sequence to the target cell, it is preferred that the plasmid be incorporated into a viral or non-viral delivery system.

1. Non-Viral Delivery Systems

Examples of non viral delivery systems used to introduce the p16 or p21 gene to the target cell include expression plasmids capable of directing the expression of the therapeutic gene of interest in the target cell. Expression plasmids are autonomously replicating, extrachromosomal circular DNA molecules, distinct from the normal genome and nonessential for cell survival under nonselective conditions capable of effecting the expression of a DNA sequence in the target cell. Plasmids autonomously replicate in bacteria to facilitate bacterial production, but it is not necessary that such plasmids containing the cyclin dependent kinase gene replicate in the target cell in order to achieve the therapeutic effect. The transgene may also be under control of a tissue specific promoter region allowing expression of the transgene only in particular cell types. Those of skill in the art will readily appreciate the variety of expression plasmids which may be useful in the practice of the present invention.

The expression plasmid may also contain promoter, enhancer or other sequences aiding expression of the therapeutic gene and/or secretion can also be included in the expression vector. Additional genes, such as those encoding drug resistance, can be included to allow selection or screening for the presence of the recombinant vector. Such additional genes can include, for example, genes encoding neomycin resistance, multi-drug resistance, thymidine kinase, beta-galactosidase, dihydrofolate reductase (DHFR), and chloramphenicol acetyl transferase.

The expression plasmid containing the therapeutic gene may be encapsulated in liposomes. Liposomes include emulsions, foams, micelles, insoluble monolayers, liquid crystals, phospholipid dispersions, lamellar layers and the like. The delivery of DNA sequences to target cells using liposome carriers is well known in the art. A variety of methods are available for preparing liposomes, as described in, e.g., Szoka et al. *Ann. Rev. Biophys. Bioeng.* 9:467 (1980), Szoka, et al. U.S. Pat. No. 4,394,448 issued Jul. 19, 1983, as well as U.S. Pat. Nos. 4,235,871, 4,501,728, 4,837,028, and 5,019,369, incorporated herein by reference. Liposomes useful in the practice of the present invention may be formed from one or more standard vesicle-forming lipids, which generally include neutral and negatively charged phospholipids and a sterol, such as cholesterol.

Examples of such vesicle forming lipids include DC-chol, DOGS, DOTMA, DOPE, DOSPA, DMRIE, DOPC, DOTAP, DORIE, DMRIE-HP, n-spermidine cholesterol carbamate and other cationic lipids as disclosed in U.S. Pat. No. 5,650,096. The selection of lipids is generally guided by consideration of, e.g., liposome size, acid lability and stability of the liposomes in the blood stream. Additional components may be added to the liposome formulation to increase serum half-life such as polyethylene glycol coating (so called "PEG-ylation") as described in U.S. Pat. No. 5,013,556 issued May 7, 1991 and U.S Pat. No. 5,213,804 issued May 25, 1993.

In order to insure efficient delivery of the therapeutic gene to a particular tissue or organ, it may be advantageous to incorporate elements into the non-viral delivery system which facilitate cellular targeting. For example, a lipid encapsulated expression plasmid may incorporate modified surface cell receptor ligands to facilitate targeting. Although a simple liposome formulation may be administered, the liposomes either filled or decorated with a desired composition of the invention of the invention can delivered systemically, or can be directed to a tissue of interest, where the liposomes then deliver the selected therapeutic/ immunogenic peptide compositions. Examples of such ligands includes antibodies, monoclonal antibodies, humanized antibodies, single chain antibodies, chimeric antibodies or functional fragments (Fv, Fab, Fab') thereof.

Alternatively, the DNA constructs of the invention can be linked through a polylysine moiety to a targeting moiety as described in Wu, et al. U.S. Pat. No. 5,166,320 issued Nov. 24, 1992 and Wu, et al, U.S. Pat. No. 5,635,383 issued Jun. 3, 1997, the entire teachings of which are herein incorporated by reference.

2. Viral Delivery Systems

In other instances, the DNA sequence is delivered by a viral delivery system wherein the therapeutic gene of interest is incorporated into a viral genome capable of infecting the target cell and the gene is operably linked to expression and control sequences such that the gene of interest is expressed under appropriate conditions in the target cell. The vectors useful in the practice of the present invention may also be derived from the viral genomes. Vectors which may be employed include recombinantly modified enveloped or non-enveloped DNA and RNA viruses, preferably selected from baculoviridiae, parvoviridiae, picornaviridiae, herpesveridiae, poxviridae or adenoviridiae. Chimeric vectors may also be employed which exploit advantageous elements of each of the parent vector properties (See e.g., Feng, et al. (1997) *Nature Biotechnology* 15:866–870.) Such viral genomes may be modified by recombinant DNA techniques to include the cyclin dependent kinase inhibitor gene and may be engineered to be replication deficient, conditionally replicating or replication competent. In the preferred practice of the invention, the vectors are replication deficient or conditionally replicating. Preferred vectors are derived from the adenoviral, adeno-associated viral and retroviral genomes. In the most preferred practice of the invention, the vectors are replication incompetent vectors derived from the human adenovirus genome. The transgene may also be under control of a tissue specific promoter region allowing expression of the transgene only in particular cell types.

It may be valuable in some instances to utilize or design vectors to achieve introduction of the exogenous transgene in a particular cell type. Certain vectors exhibit a natural tropism for certain tissue types. For example, vectors derived from the genus herpesviridiae have been shown to have preferential infection of neuronal cells. Examples of recombinantly modified herpesviridiae vectors are disclosed in U.S. Pat. No. 5,328,688 issued Jul. 12, 1994.

In other instances, to insure efficient delivery of the therapeutic gene to a particular tissue or organ, it may be advantageous to incorporate elements into the viral delivery system which facilitate cellular targeting. Viral envelopes used for packaging the constructs of the invention can be modified by the addition of receptor ligands or antibodies specific for a receptor to permit receptor-mediated endocytosis into specific cells (e.g., WO 93/20221, WO 93/14188; WO 94/06923). In some embodiments of the invention, the DNA constructs of the invention are linked to viral proteins, such as adenovirus particles, to facilitate endocytosis. (See, e.g. Curiel, et al. (1991) Proc. Natl. Acad. Sci. U.S.A. 88:8850–8854). Cell type specificity or cell type targeting may also be achieved in vectors derived from viruses having characteristically broad infectivities by the modification of the viral envelope proteins. For example, cell targeting has been achieved with adenovirus vectors by selective modification of the viral genome knob and fiber coding sequences to achieve expression of modified knob and fiber domains having specific interaction with unique cell surface receptors. Examples of such modifications are described in Wickham, et al. (1997) J. Virol. 71 (11):8221–8229 (incorporation of RGD peptides into adenoviral fiber proteins); Arnberg, et al. (1997) Virology 227:239–244 (modification of adenoviral fiber genes to achieve tropism to the eye and genital tract); Harris and Lemoine (1996) TIG 12(10):400–405; Stevenson, et al. (1997) J. Virol. 71(6): 4782–4790; Michael, et al. (1995) Gene Therapy 2:660–668 (incorporation of gastrin releasing peptide fragment into adenovirus fiber protein); and Ohno, et al. (1997) Nature Biotechnology 15:763–767 (incorporation of Protein A-IgG binding domain into Sindbis virus). Also see U.S. Pat. Nos. 5,721,126 and 5,559,099, herein incorporated by reference. Other methods of cell specific targeting have been achieved by the conjugation of antibodies or antibody fragments to the envelope proteins (see, e.g., Michael, et al. (1993) J. Biol. Chem. 268:6866–6869, Watkins, et al. (1997) Gene Therapy 4:1004–1012; Douglas, et al. (1996) Nature Biotechnology 14:1574–1578. Alternatively, particular moieties may be conjugated to the viral surface to achieve targeting (See, e.g. Nilson, et al. (1996) Gene Therapy 3:280–286 (conjugation of EGF to retroviral proteins)).

Conditionally replicating viral vectors are used to achieve selective expression in particular cell types while avoiding untoward broad spectrum infection. Examples of conditionally replicating vectors are described in Bischoff, et al. (1996) Science 274:373–376; Pennisi, E. (1996) Science 274:342–343; Russell, S. J. (1994) Eur. J. of Cancer 30A (8):1165–1171. Additionally, the viral genome may be modified to include inducible promoters which achieve replication or expression of the transgene only under certain conditions. Examples of inducible promoters are known in the scientific literature (See, e.g. Yoshida and Hamada (1997) Biochem. Biophys. Res. Comm. 230:426–430; Iida, et al. (1996) J. Virol. 70(9):6054–6059; Hwang, et al. (1997) J. Virol. 71(9):7128–7131; Lee, et al. (1997) Mol. Cell. Biol. 17(9):5097–5105; and Dreher, et al. (1997) J. Biol. Chem. 272(46); 29364–29371). The transgene may also be under control of a tissue specific promoter region allowing expression of the transgene only in particular cell types.

In some instances, particularly when employing a conditionally replicating or replication competent vector, it may be desirable to include a suicide gene in the viral vector in addition to the therapeutic gene. A suicide gene is a nucleic acid sequence, the expression of which renders the cell susceptible to killing by external factors or causes a toxic condition in the cell. A well known example of a suicide gene is the thymidine kinase (TK) gene (see e.g. Woo, et al. U.S. Pat. No. 5,631,236 issued May 20, 1997 and Freeman, et al. U.S. Pat. No. 5,601,818 issued Feb. 11, 1997) in which the cells expressing the TK gene product are susceptible to selective killing by the administration of gancyclovir. This provides a "safety valve" to the viral vector delivery system to prevent widespread infection due to the spontaneous generation of fully replication competent viral vectors of broad range infectivity.

In the preferred practice of the invention, the vector is derived from genus adenoviridiae. Particularly preferred vectors are derived from the human adenovirus type 2 or type 5. Such vectors are preferably are replication deficient by modifications or deletions in the E1a and/or E1b coding regions. Other modifications to the viral genome to achieve particular expression characteristics or permit repeat administration or lower immune response are preferred. More preferred are recombinant adenoviral vectors having complete or partial deletions of the E4 coding region, optionally retaining (or deleting) E4 ORF6 and ORF 6/7. The E3 coding sequence has been demonstrated to be nonessential and may be deleted from adenoviral vectors but is preferably retained. In particular, it is preferred that the promoter operator region of E3 be modified to increase expression of E3 to achieve a more favorable immunological profile for the therapeutic vectors. Most preferred are human adenoviral type 5 vectors containing a DNA sequence encoding a cyclin dependent kinase inhibitor under control of the cytomegalovirus promoter region and the tripartite leader sequence having E3 under control of the CMV promoter and deletion of E4 coding regions while retaining E4 ORF6 and ORF 6/7. In the most preferred practice of the invention as exemplified herein, the cyclin dependent kinase inhibitor is p16 or p21.

3. Protein Delivery Systems

Alternatively to viral or non-viral delivery of p16 or p21 coding sequences, the p16 or p21 protein may also be administered directly. When the protein is to be administered directly, it is preferred that the protein be incorporated into a formulation which facilitates or enhances the uptake of the protein into the target ocular cell.

Formulations may include excipients which stabilize polypeptides, such as methionine (U.S. Pat. No. 5,358,708); osmolytes, lyotropic salts, water-soluble synthetic and natural polymers, surfactants, sulfated polysaccharides, proteins, and buffers (U.S. Pat. No. 5,580,856); fatty acids, amino acids, vitamins (U.S. Pat. No. 5,078,997), and so on.

D. Pharmaceutical Formulation

The invention further provides pharmaceutical formulations comprising the therapeutic gene in a viral or non-viral delivery system for administration. The compositions of the invention will be formulated for administration by manners known in the art acceptable for administration to a mammalian subject, preferably a human. In particular delivery systems may be formulated for intramuscular, intravenous, injectable depot type devices or topical administration.

The compositions of the invention can also be administered in topical formulations or polymer matrices, hydrogel matrices, polymer implants, or encapsulated formulations to allow slow or sustained release of the compositions. A particularly preferred formulation is a suspension or solution of the delivery system in a topical ocular formulation, such as eye drops.

1. Carriers

When the delivery system is formulated as a solution or suspension, the delivery system is in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of the compositions of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

2. Delivery Enhancers

The pharmaceutical formulations of the invention may optionally include one or more delivery-enhancing agents, The term "delivery enhancing agents" includes agents which facilitate the transfer of the nucleic acid or protein molecule to the target cell. Examples of such delivery enhancing agents detergents, alcohols, glycols, surfactants, bile salts, heparin antagonists, cyclooxygenase inhibitors, hypertonic salt solutions, and acetates. Alcohols include for example the aliphatic alcohols such as ethanol, N-propanol, isopropanol, butyl alcohol, acetyl alcohol. Glycols include glycerine, propyleneglycol, polyethyleneglycol and other low molecular weight glycols such as glycerol and thioglycerol.

Acetates such as acetic acid, gluconic acid, and sodium acetate are further examples of delivery-enhancing agents.

Hypertonic salt solutions like 1M NaCl are also examples of delivery-enhancing agents. Examples of surfactants are sodium dodecyl sulfate (SDS) and lysolecithin, polysorbate 80, nonylphenoxypolyoxyethylene, lysophosphatidyl-choline, polyethylenglycol 400, polysorbate 80, polyoxyethylene ethers, polyglycol ether surfactants and DMSO. Bile salts such as taurocholate, sodium tauro-deoxycholate, deoxycholate, chenodesoxycholate, glycocholic acid, glyco-chenodeoxycholic acid and other astringents like silver nitrate may be used. Heparin-antagonists like quaternary amines such as protamine sulfate may also be used. Cyclooxygenase inhibitors such as sodium salicylate, salicylic acid, and non-steroidal antiinflammatory drug (NSAIDS) like indomethacin, naproxen, diclofenac may be used.

Detergents include anionic, cationic, zwitterionic, and nonionic detergents. Exemplary detergents include but are not limited to taurocholate, deoxycholate, taurodeoxycholate, cetylpyridium, benalkonium chloride, ZWITTERGENT®3-14 detergent, CHAPS (3-{(3-Cholamidopropyl)dimethylammoniol}-1-propanesulfonate hydrate, Aldrich), Big CHAP, Deoxy Big CHAP, TRITON®-X-100 detergent, C12E8, Octyl-B-D-Glucopyranoside, PLURONIC®-F68 detergent, TWEEN® 20 detergent, and TWEEN® 80 detergent (CALBIOCHEM® Biochemicals).

The concentration of the delivery-enhancing agent will depend on a number of factors known to one of ordinary skill in the art such as the particular delivery-enhancing agent being used, the buffer, pH, target tissue or organ and mode of administration. The concentration of the delivery-enhancing agent will be in the range of 1% to 50% (v/v), preferably 10% to 40% (v/v) and most preferably 15% to 30% (v/v). Preferably, the detergent concentration in the final formulation administered to the patient is about 0.5–2× the critical micellization concentration (CMC).

In order to facilitate the improved gene transfer for nucleic acid formulations comprising commercial Big-CHAP preparations, the concentration of Big CHAP will vary based on its commercial source. When the Big CHAP is sourced from CALBIOCHEM®, it is preferred that the concentration be in a range of 2 to 10 millimolar. More preferred is 4 to 8 millimolar. Most preferred is approximately 7 millimolar.

When the Big CHAP is sourced from Sigma, it is preferred that the concentration of Big CHAP be in a range of 15 to 35 millimolar. More preferred is 20 to 30 millimolar. Most preferred is approximately 25 millimolar.

In a further embodiment of the invention, delivery-enhancing agents having Formula I are provided:

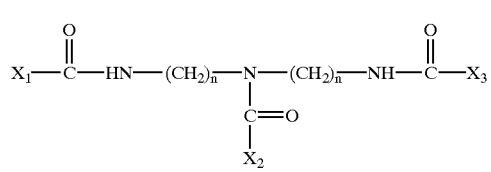

wherein n is an integer from 2–8, X1 is a cholic acid group or deoxycholic acid group, and X2 and X3 are each independently selected from the group consisting of a cholic acid group, a deoxycholic acid group, and a saccharide group. At least one of X2 and X3 is a saccharide group. The saccharide group may be selected from the group consisting of pentose monosaccharide groups, hexose monosaccharide groups, pentose-pentose disaccharide groups, hexose-hexose disaccharide groups, pentose-hexose disaccharide groups, and hexose-pentose disaccharide groups. In one preferred embodiment, the compounds of the present invention have the Formula II:

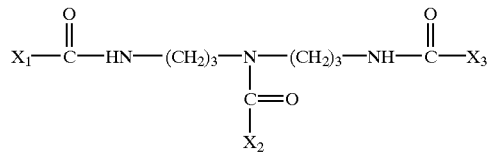

wherein X1 and X2 are selected from the group consisting of a cholic acid group and a deoxycholic acid group and X3 is a saccharide group.

These compounds are preferably used in the range of about 0.002 to 2 mg/ml, more preferably about 0.02 to 2 mg/ml, most preferably about 0.2 to 2 mg/ml in the formulations of the invention. Most preferred is approximately 2 mg/ml.

Phosphate buffered saline (PBS) is the preferred solubilizing agent for these compounds. However, one of ordinary skill in the art will recognize that certain additional excipients and additives may be desirable to achieve solubility characteristics of these agents for various pharmaceutical formulations. For example, the addition of well known solubilizing agents such as detergents, fatty acid esters, surfactants may be added in appropriate concentrations so as to facilitate the solubilization of the compounds in the various solvents to be employed. When the solvent is PBS, a preferred solubilizing agent is Tween 80 at a concentration of approximately 0.15%.

These delivery-enhancing compounds may be used alone, in combination with each other, or in combination with another delivery-enhancing agent.

E. Diseases Amenable to Treatment

The formulations of the present invention are useful in the treatment of ocular diseases. The term ocular diseases includes but is not limited to diseases of the eye associated with the hyperproliferation cells in the eye. Examples of hyperproliferative disorders include glaucoma surgery failure and proliferative vitreoretinopathy. Other ocular diseases associated with excessive angiogenesis such as age related macular degeneration, retinopathy of prematurity, and diabetic retinopathy may also be treated in accordance with the practice of the present invention.

Proliferative vitreoretinopathy describes a condition whereby the retina of eye is pulled away from the wall of the eye caused by a hyperproliferation of cells of the retinal pigmented epithelium in response to the injury which caused the retinal detachment. Subsequent contraction of the cellular membrane in the time course of proliferative vitreoretinopathy is a primary cause of failure of retinal reattachment surgery.

Glaucoma results from an abnormally high pressure in the eye. The commonly accepted surgical treatment for glaucoma is to provide a drain for excess vitreous humor from the eye to relieve the excess pressure. A significant complication of this surgery results from the reocclusion of the drain site from the hyperproliferation of the fibroblasts resulting in repeated surgical intervention.

The present invention provides methods and compositions for the treatment of "glaucoma surgery failure" by administration of p21 or p16 prevent hyperproliferation in these tissues surrounding the drainage site to prevent the occlusion of the drainage duct.

F. Methods of Administration

The therapeutic agents of the invention can be introduced into the tissue of interest in vivo or ex vivo by a variety of methods. In some embodiments of the invention, the therapeutic agent is introduced to cells by such methods as liposome fusion, injection, topically or biolistics. In some embodiments of the invention, the compositions of the invention can be administered directly into the eye, such as to the intraophthalmic artery, subretinal, intravitreal or subconjunctival space. The formulations of the present invention may be administered to subconjunctival and scleral tissues at the time of surgery, preferably in the form of topical drop formulations or with depot devices such as a gel foam (Weck cell) sponge. Additionally, the formulations of the present invention may be administered following surgery, by subconjuctival injection. The formulations of the present invention may be administered in a single dose or in multiple doses. Preferably, when doses are administered, the factor determining the frequency of repeat administration is the duration of transgene expression.

In the case of glaucoma surgery failure and proliferative vitreoretinopathy, the formulations of the present invention are preferably administered at the time of surgery. In the case of angiogenic diseases such as age related macular degeneration and diabetic retinopathy, the formulations of the present invention are administered over a course of treatment ranging from weeks to years. The preferred routes of administration for the treatment of such diseases include ophthalmic artery administration, subretinal injection, intravitreal injection. Sustained release formulations such as implants would also be appropriate for the treatment of such long term disease indications. These formulations may also be administered in combination with other anti-angiogenic agents.

Subretinal injections for the treatment of retinal proliferative disease, especially proliferative vitreoretinopathy. This procedure may be performed before, during or after surgery, preferably during the surgical procedure.

Alternatively, angiogenic or proliferative diseases of the eye (especially the cells of the retinal pigment epithelium) may be treated by the intra-arterial, or subretinal, administration of viral or non-viral formulations of the present invention. In particular, viral or non-viral formulations may be delivered via the opthalmic artery to enhance delivery to the target tissue.

1. Therapy

In one embodiment of the invention, a DNA sequence encoding a cyclin dependent kinase inhibitor such as p27kip, p57kip2, p15ink4b, p18ink4c, p19ink4d p16ink4a or p21sdi is administered to the eye. In some embodiments the cyclin dependent kinase inhibitor gene or polypeptide is provided in combination with each other and/or one or more of the following genes or proteins: p53, RB, a suicide gene or gene product.

In some embodiments of the invention, the formulations of the present invention may also be administered in combination with other chemotherapeutic agents. Examples of chemotherapeutic agents useful in the practice of the present invention includes fluorouracil and mitomycin-C. Additional agents, such corticosteroids, may also be administered in the course therapy.

In some embodiments of the invention, therapeutic polypeptides of the invention are administered directly to a patient in need of treatment. A "therapeutically effective" dose is an amount of therapeutic gene or polypeptide sufficient to prevent or reduce severity of the pathogeneis of the disease.

In some embodiments of the invention, the compositions of the invention are administered ex vivo to cells or tissues explanted from a patient, then returned to the patient. Examples of ex vivo administration of therapeutic gene constructs include Arteaga et al. (1996) *Cancer Research* 56(5):1098–1103; Nolta et al. (1996) *Proc. Natl. Acad. Sci. U.S.A.* 93(6):2414–9; Koc et al. (1996) *Seminars in Oncology* 23(1):46–65; Raper et al. (1996) *Annals of Surgery* 223(2):116–26; Dalesandro et al. (1996) *J. Thorac. Cardi. Surg.* 11(2):416–22; and Makarov et al. (1996) *Proc. Natl. Acad. Sci. U.S.A.* 93(1):402–6.

G. Dosage Ranges

Therapeutically effective amounts of the pharmaceutical composition comprising a therapeutic gene, such as p16 or p21 in a recombinant viral vector delivery system formulated in a buffer comprising a delivery-enhancing agent will be administered in accord with the teaching of this invention. For example, therapeutically effective amounts of the p16 or p21 cyclin dependent kinase inhibitor gene in a recombinant adenoviral vector formulated in a buffer optionally containing a delivery-enhancing agent are in the range of about $1 \times 10^8$ particles/ml to $1 \times 10^{12}$ particles/ml, more typically about $1 \times 10^8$ particles/ml to $5 \times 10^{11}$ particles/ml, most typically $1 \times 10^9$ particles/ml to $1 \times 10^{11}$ particles/ml (PN/ml).

EXAMPLES

The following examples provide the methodology and results of experiments demonstrating the recombinant adenoviruses (rAd) that express the p16 and/or p21 cell cycle control genes to inhibit proliferation of target cells. As will be apparent to those skilled in the art to which the invention pertains, the present invention may be embodied in forms other than those specifically disclosed above, without departing from the spirit or essential characteristics of the invention. The particular embodiments of the invention described below, are therefore to be considered as illustrative and not restrictive.

The following examples are intended to illustrate, not limit the scope of this invention. In the following examples, "g" means grams, "ml" means milliliters, "mol" means moles, "EC" means degrees Centigrade, "min." means minutes, "FBS" means fetal bovine serum, and "PN" specifies particle number. All temperatures are in degrees Centigrade unless otherwise specified.

Example 1

Construction of Recombinant Adenoviral Vectors

Recombinant adenoviruses were constructed to express the p16 and p21 coding sequences following infection of primary ocular fibroblasts. The DNA sequence encoding p16 employed in the construction of the present recombinant adenoviral vectors was (SEQ ID No: 1):

```
ATG GAG CCT TCG GCT GAC TGG CTG GCC ACG GCC GCG
GCC CGG GGT CGG GTA GAG GAG GTG CGG GCG CTG CTG
GAG GCG GGG GCG CTG CCC AAC GCA CCG AAT AGT TAC
GGT CGG AGG CCG ATC CAG GTC ATG ATG ATG GGC AGC
GCC CGA GTG GCG GAG CTG CTG CTG CTC CAC GGC GCG
GAG CCC AAC TGC GCC GAC CCC GCC ACT CTC ACC CGA
CCC GTG CAC GAC GCT GCC CGG GAG GGC TTC CTG GAC
ACG CTG GTG GTG CTG CAC CGG GCC GGG GCG CGG CTG
GAC GTG CGC GAT GCC TGG GGC CGT CTG CCC GTG GAC
CTG GCT GAG GAG CTG GGC CAT CGC GAT GTC GCA CGG
TAC CTG CGC GCG GCT GCG GGG GCC ACC AGA GGC AGT
AAC CAT GCC CGC ATA GAT GCC GCG GAA GGT CCC TCA
GAC ATC CCC GAT TGA
```

The DNA sequence encoding p21 employed in the construction of the present recombinant adenoviral vectors was as follows (SEQ ID No: 4):

```
ATG TCA GAA CCG GCT GGG GAT GTC CGT CAG AAC CCA
TGC GGC AGC AAG GCC TGC CCC CGC CTC TTC GGC CCA
GTG GAC AGC GAG CAG CTG AGC CGC GAC TGT GAT GCG
CTA ATG GCG GGC TGC ATC CAG GAG GCC CGT GAG CGA
TGG AAC TTC GAC TTT GTC ACC GAG ACA CCA CTG GAG
GGT GAC TTC GCC TGG GAG CGT GTG CGG GGC CTT GGC
CTG CCC AAG CTC TAC CTT CCC ACG GGG CCC CGG CGA
GGC CGG GAT GAG TTG GGA GGA GGC AGG CGG CCT GGC
ACC TCA CCT GCT CTG CTG CAG GGG ACA GCA GAG GAA
GAC CAT GTG GAC CTG TCA CTG TCT TGT ACC CTT GTG
CCT CGC TCA GGG GAG CAG GCT GAA GGG TCC CCA GGT
GGA CCT GGA GAC TCT CAG GGT CGA AAA CGG CGG CAG
ACC AGC ATG ACA GAT TTC TAC CAC TCC AAA CGC CGG
CTG ATC TTC TCC AAG AGG AAG CCC TAA
```

The DNA sequence encoding p56-RB employed in the construction of the present recombinant adenoviral vectors was as follows (SEQ ID No: 6):

```
ATG AAC ACT ATC CAA CAA TTA ATG ATG ATT TTA AAT
TCT GCA AGT GAT CAA CCT TCA GAA AAT CTG ATT TCC
TAT TTT AAC AAC TGC ACA GTG AAT CCA AAA GAA AGT
ATA CTG AAA AGA GTG AAG GAT ATA GGA TAC ATC TTT
AAA GAG AAA TTT GCT AAA GCT GTG GGA CAG GGT TGT
GTC GAA ATT GGA TCA CAG CGA TAC AAA CTT GGA GTT
CGC TTG TAT TAC CGA GTA ATG GAA TCC ATG CTT AAA
TCA GAA GAA GAA CGA TTA TCC ATT CAA AAT TTT AGC
AAA CTT CTG AAT GAC AAC ATT TTT CAT ATG TCT TTA
TTG GCG TGC GCT CTT GAG GTT GTA ATG GCC ACA TAT
AGC AGA AGT ACA TCT CAG AAT CTT GAT TCT GGA ACA
GAT TTG TCT TTC CCA TGG ATT CTG AAT GTG CTT AAT
TTA AAA GCC TTT GAT TTT TAC AAA GTG ATC GAA AGT
TTT ATC AAA GCA GAA GGC AAC TTG ACA AGA GAA ATG
ATA AAA CAT TTA GAA CGA TGT GAA CAT CGA ATC ATG
GAA TCC CTT GCA TGG CTC TCA GAT TCA CCT TTA TTT
GAT CTT ATT AAA CAA TCA AAG GAC CGA GAA GGA CCA
ACT GAT CAC CTT GAA TCT GCT TGT CCT CTT AAT CTT
CCT CTC CAG AAT AAT CAC ACT GCA GCA GAT ATG TAT
CTT TCT CCT GTA AGA TCT CCA AAG AAA AAA GGT TCA
ACT ACG CGT GTA AAT TCT ACT GCA AAT GCA GAG ACA
CAA GCA ACC TCA GCC TTC AGA CC CAG AAG CCA TTG
AAA TCT ACC TCT CTT TCA CTG TTT TAT AAA AAA GTG
TAT CGG CTA GCC TAT CTC CGG CTA AAT ACA CTT TGT
GAA CGC CTT CTG TCT GAG CAC CCA GAA TTA GAA CAT
ATC ATC TGG ACC CTT TTC CAG CAC ACC CTG CAG AAT
GAG TAT GAA CTC ATG AGA GAC AGG CAT TTG GAC CAA
ATT ATG ATG TGT TCC ATG TAT GGC ATA TGC AAA GTG
AAG AAT ATA GAC TTA AAA TTC AAA ATC ATT GTA ACA
GCA TAC AAG GAT CTT CCT CAT GCT GTT CAG GAG ACA
TTC AAA CGT GTT TTG ATC AAA GAA GAG GAG TAT GAT
TCT ATT ATA GTA TTC TAT AAC TCG GTC TTC ATG CAG
```

-continued

```
AGA CTG AAA ACA AAT ATT TTG CAG TAT GCT TCC ACC

AGG CCC CCT ACC TTG TCA CCA ATA CCT CAC ATT CCT

CGA AGC CCT TAC AAG TTT CCT AGT TCA CCC TTA CGG

ATT CCT GGA GGG AAC ATC TAT ATT TCA CCC CTG AAG

AGT CCA TAT AAA ATT TCA GAA GGT CTG CCA ACA CCA

ACA AAA ATG ACT CCA AGA TCA AGA ATC TTA GTA TCA

ATT GGT GAA TCA TTC GGG ACT TCT GAG AAG TTC CAG

AAA ATA AAT CAG ATG GTA TGT AAC AGC GAC CGT GTG

CTC AAA AGA AGT GCT GAA GGA AGC AAC CCT CCT AAA

CCA CTG AAA AAA CTA CGC TTT GAT ATT GAA GGA TCA

GAT GAA GCA GAT GGA AGT AAA CAT CTC CCA GGA GAG

TCC AAA TTT CAG CAG AAA CTG GCA GAA ATG ACT TCT

ACT CGA ACA CGA ATG CAA AAG CAG AAA ATG AAT GAT

AGC ATG GAT ACC TCA AAC AAG GAA GAG AAA TGA
```

A viral vector backbone was created based on a human adenovirus type 5 genome comprising deletions of the E1a and E1b and protein IX gene functions and partial deletion of the E4 coding region (retaining the function of the E4 orf 6 and E4 orf 6/7 genes). The recombinant viral vectors for expression of p16 and p21 were constructed as described in Wang, et al. (1997) *Cancer Research* 57:351–354. The recombinant viral vectors for expression of p56 was constructed as described in Smith, et al. (1997) *Circulation* 96(6):1899–1905. This sequence was inserted into the viral vector backbone so as to be under control of the CMV promoter element. The resulting vector was designated QLCC.

Example 2
Preparation of Target Cells

Human ocular fibroblast were used in in vitro assays as they are the cellular component causing pathology in glaucoma surgery failure. Primary ocular fibroblast cell lines from three different human sources (HOF-gon, HOF-nep and HOF-sch) were obtained from by Drs. S. Schwartz, D. Farber, and S. Ogueta, Jules Stein Eye Institute, University of California Los Angeles. Cells were synchronized in G1 by incubation in low serum containing HAMs F12/DME media (commercially available from Irvine Scientific, Irvine California) containing 0.5% FBS for a period of 3 days.

Example 3
Evaluation of Activity in a Human Ocular Fibroblasts Model

Human ocular fibroblast cells (prepared in substantial accordance with the teaching of Example 2 above) were infected with rAd constructs (prepared in substantial accordance with the teaching of Example 1 above) in low serum media (F12/DME media containing 0.5% FBS) for 20–24 h with a dose of either $5\times10^8$ and $5\times10^9$ adenoviral particles.

The cells were stimulated to enter the cell cycle by incubation in complete media (10% FBS) and assayed 18–24 hours after stimulation. Response to rAd mediated gene expression was measured by 3H-thymidine incorporation or by BrdU incorporation. Plates were rinsed and re-fed with complete media (10% FBS). 16 h after release BrdU was added for 5 h and cells were harvested and analyzed by FACS for BrdU incorporation (DNA synthesis) and PI staining (DNA content). Cells that had incorporated BrdU were stained using a FITC conjugated mAb to BrdU (commercially available from Becton-Dickinson) and detected by FACS analysis.

Figure 1B:
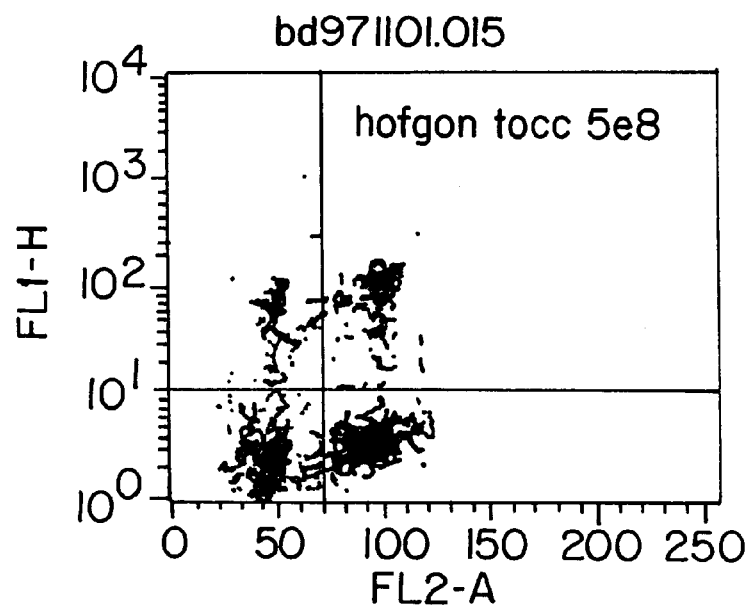
FIG. 1B represents the response of hofgon cells to a dose of $5 \times 10^8$ ZZCC viral particles (rAd-null).

Bivariate analysis on DNA content and BrdU positive cells was used to analyze the data. The response to treatment comparing Ad-null (ZZCC) with rAd-p21 (TOCC) are represented in the two-dimensional plot is shown in FIG. 1. The X-axis (FL2-A) corresponds to propidium iodide (PI) staining or DNA content. The Y-axis (FL1-H) corresponds to FITC staining or BrdU incorporation. Therefore, in the lower right quadrant are cells that did not exit G1 phase during labeling with BrdU. The cells in the arc from the lower left to the upper right quadrants represent cells in the process of BrdU incorporation at the time of harvest. Cells in the upper left quadrant had incorporated BrdU during the labeling period and then divided.

Figure 2:
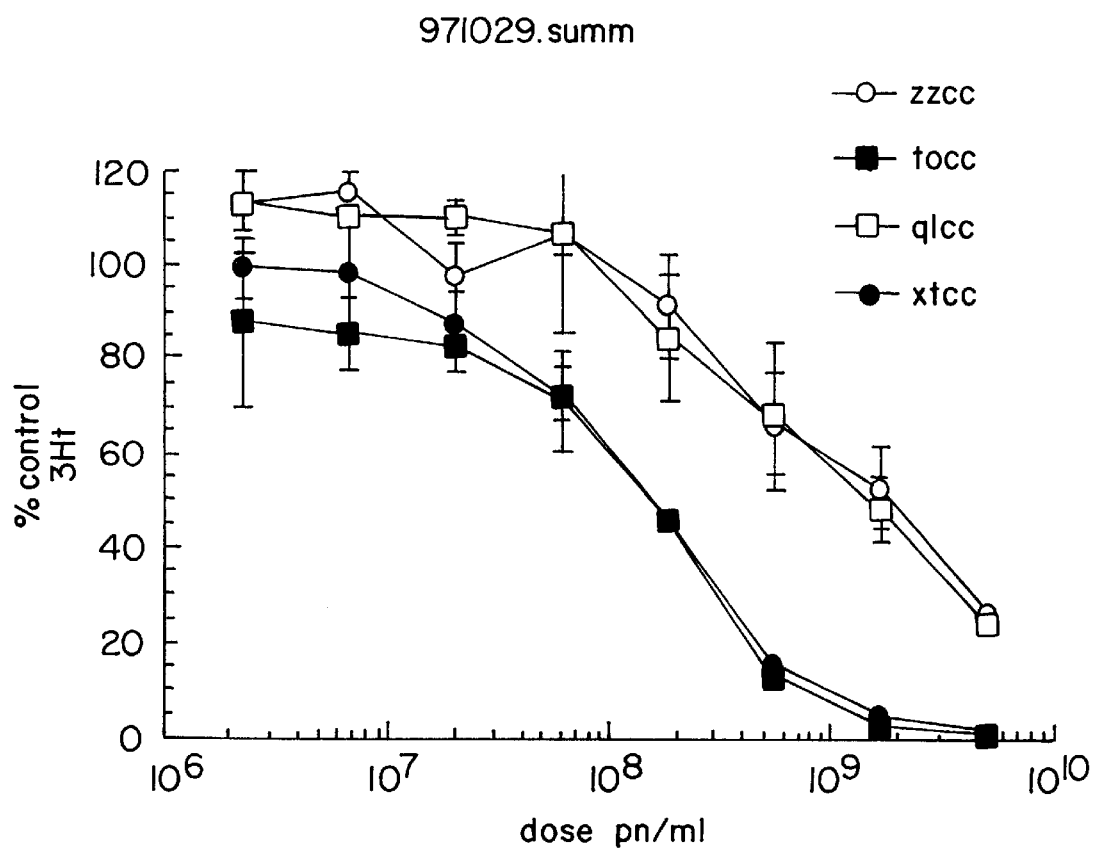
FIG. 2 is a graph representing the 3H-thymidine incorporation in fibroblasts exposed to recombinant adenoviruses incorporating p16 (XTCC), p21 (TOCC) and RB56 (QLCC) sequences and null control vector (ZZCC).

The percent of cells remaining in G1 was determined from the lower left quadrant. The percent of cells in S phase was determined from the both upper quadrants and therefore represent the percent cells in S-phase during labeling. The cells in the lower right quadrant are labeled G2. Two doses of virus were tested, $5\times10^8$ and $5\times10^9$ particles per ml of media. The from the analysis of human ocular fibroblasts (HOF-) from 3 human donors (GON, NEP and SCH) and data is summarized in Table 1 above. Dose response to rAd treatment measured by tritiated thymidine incorporation shown in FIG. 2.

Example 4
Construction of Additional Viral Vectors

A viral vector backbone was created based on a human adenovirus type 5 genome comprising deletions of the E1a and E1b and protein IX gene functions and partial deletion of the E3 coding region. Specifically, the deletions of base pairs 355 to 3325was used to eliminate E1a and E1b functions, deletion of base pairs 3325 to 4021 was used to eliminate protein IX function and deletions of 28592 to 30470 were used to eliminate E3 functions. See Wills, et al. (1994) *Human Gene Therapy* 5:1079–1088. The DNA sequence encoding the cytomegalovirus immediate early promoter without the presence of the CMV promoter intron was inserted into the rAd viral genome. This vector without an exogenous transgene was used as control vector and was designated ZZCB.

The green fluorescent protein (GFP) coding sequence was obtained as a NheI to BclI restriction endonuclease cleavage fragment from the vector pEGFP-C1 (commercially available from CloneTech). This sequence was inserted into the XbaI to BamHI site of the resulting vector was designated GFCB.

The recombinant viral vectors for expression of p53 were constructed as described in Wills, et al., supra.

Example 5
Comparison of p53, p56RB and p21 Activity

Human Ocular Fibroblast (HOF) cells obtained from 2 human donors (HOFtol and HOFcar) were prepared in substantial accordance with Example 2 above. The GFCB and FTCB virus constructions prepared in accordance with the teaching of Example 4 were tested in comparison with the previously constructed p16 and p56RB vectors prepared in accordance with Example 1. Two doses of virus were tested, $1\times10^8$ and $1\times10^9$ particles per ml of media 24 h. Plates were rinsed and re-fed with complete media (10% FBS). 16 h after release BrdU was added for 5 h and cells were harvested and analyzed by FACS for BrdU incorporation (DNA synthesis) and PI staining (DNA content).

Controls included untreated cells released (ut 10). In addition to cell cycle analysis the percent of gfcb treated cells expressing GFP (green fluorescent protein) transgene was determined by FACS immediately after cells were harvested. The percent of cells that incorporated BrdU during the labeling period (16–21 h post-release) is reported as %s.

Results

Serum starved human ocular fibroblast were treated with rAd for 24 h then rAd was washed. Cells were released from quiescence by feeding cells with complete media and cells were harvested 21 h later for analysis of transgene expression by FACS. Treatment with $1\times10^8$ pn/ml resulted in 62% and 79% positive cells in HOF-TOL and HOF-CAR respectively. A dose of $1\times10^9$ resulted in 100% of the cells expressing GFP transgene for both HOF-TOL and HOF-CAR. Cell cycle analysis of cells is tabulated in Table 2 above.

As will be apparent to those skilled in the art to which the invention pertains, the present invention may be embodied in forms other than those specifically disclosed above, without departing from the spirit or essential characteristics of the invention. The particular embodiments of the invention described above, are, therefore to be considered as illustrative and not restrictive. The scope of the present invention is as set forth in the appended claims rather than being limited to the examples contained in the foregoing description.

What is claimed is:

1. A method for ameliorating glaucoma surgery failure in a mammal, the method comprising administering to an eye of said mammal during or after glaucoma surgery a nucleotide sequence encoding a p21 cyclin dependent kinase inhibitor, wherein the proliferation of ocular fibroblasts in said eye is inhibited so as to ameliorate said glacoma surgery failure.

2. The method of claim 1, wherein the nucleotide sequence is administered in a viral vector and is expressed in a cell.

3. The method of claim 2 wherein the viral vector is an adenoviral vector.

4. The method of claim 3 wherein the adenoviral vector is a human adenovirus type 5 vector.

5. The method of claim 4 wherein the human adenovirus vector is a replication deficient adenoviral vector.

6. The method of claim 5 wherein the replication deficient vector is deleted in the E4 region.

7. The method of claim 6 wherein the vector retains E4 orf 6 and E4 orf 6/7 but does not encode functional E4 peptide.

8. The method of claim 1, wherein the nucleotide sequence is administered to an ophthalmic artery, a subretinal space, a vitreal space, or a subconjunctival space.

9. The method of claim 1, wherein the nucleotide sequence is administered topically.

10. The method of claim 9, wherein the nucleotide sequence is administered in a topical drop formulation.

11. The method of claim 1, wherein the nucleotide sequence is administered in a depot device.

12. The method of claim 11, wherein the depot device comprises a sponge.

13. The method of claim 1, wherein the nucleotide sequence is administered in a non-viral delivery system.

14. The method of claim 13, wherein the nucleotide sequence is administered in a liposome.

15. The method of claim 1, wherein the nucleotide sequence is administered as a naked plasmid.

16. The method of claim 1 wherein the nucleotide sequence encoding the p21 cyclin dependent kinase inhibitor is present on an adenoviral vector.

17. A method for inhibiting proliferation of ocular fibroblasts in a mammal, the method comprising administering to an eye of said mammal a p21 cyclin dependent kinase inhibitor or a nucleotide sequence that encodes a p21 cyclin dependent kinase inhibitor, whereby the proliferation of ocular fibroblasts in said eye is inhibited.

18. A method for ameliorating glaucoma surgery failure in a mammal, the method comprising administering to an eye of said mammal during or after glaucoma surgery a p21 cyclin dependent kinase inhibitor, wherein the proliferation of ocular fibroblasts in said eye is inhibited so as to ameliorate said glacoma surgery failure.

19. The method of claim 18, wherein the cyclin dependent kinase inhibitor is administered to the eye at the time of the glaucoma surgery.

20. The method of claim 18, wherein the cyclin dependent kinase inhibitor is administered as a polypeptide.

21. The method of claim 18, wherein the cyclin dependent kinase inhibitor is administered as a nucleotide sequence that encodes the cyclin dependent kinase inhibitor.

22. The method of claim 21, wherein the nucleotide sequence is administered in a viral vector.

23. The method of claim 22, wherein the viral vector is an adenoviral vector.

24. The method of claim 23, wherein the adenoviral vector is TOCC or XTCC.

25. The method of claim 18 wherein the p21 cyclin dependent kinase inhibitor is administered on a sponge depot.

* * * * *

(12) EX PARTE REEXAMINATION CERTIFICATE (5582nd)
United States Patent
Demers

(10) Number: US 6,489,305 C1
(45) Certificate Issued: Oct. 24, 2006

(54) METHODS AND COMPOSITIONS FOR THE TREATMENT OF OCULAR DISEASES

(75) Inventor: G. William Demers, San Diego, CA (US)

(73) Assignee: Canji, Inc., San Diego, CA (US)

Reexamination Request:
No. 90/007,466, Mar. 16, 2005

Reexamination Certificate for:
| | |
|---|---|
| Patent No.: | 6,489,305 |
| Issued: | Dec. 3, 2002 |
| Appl. No.: | 09/075,505 |
| Filed: | May 8, 1998 |

(51) Int. Cl.
*A01N 43/04* (2006.01)
*A61K 31/70* (2006.01)

(52) U.S. Cl. .................. 514/44; 424/93.2; 435/320.1
(58) Field of Classification Search .............. None
See application file for complete search history.

(56) References Cited

U.S. PATENT DOCUMENTS 5,863,904 A * 1/1999 Nabel et al. .............. 514/44

FOREIGN PATENT DOCUMENTS

WO   WO 95/06415 A1   3/1995

OTHER PUBLICATIONS

Recombinant DNA Advisory Committee, Minutes of Meeting, Dec. 3–4, 2003. Section XI: Discussion of human gene transfer protocol #0307–589: A Phase I study in glaucoma subjects receiving SCH 412499 (rAd–p21) administered as a single injection into the subconjunctival space prior to primary trabeculectomy.*

Atreides et al. (2004) Wound healing modulation in glaucoma filtering surgery. International Ophthalmology Clinics 44(2): 61–106.*

Perkins et al. (2002) Adenovirus–mediated gene therapy using human p21(WAF–1/Cip–1) to prevent wound healing in a rabbit model of glaucoma filtration surgery. Archives of Ophthalmology 120(7): 941–949.*

Wen et al. (2003) Characterization of adenovirus p21 gene transfer, biodistribution, and immune response after local ocular delivery in New Zealand white rabbits. Experimental Eye Research 77: 355–365.*

Al–Aswad et al. (1996) Inhibition of fibroblast proliferation and enhancement of glaucoma filtration surgery in the rabbit with cytosine arabinoside. Investigative Ophthalmology and Visual Science 37(3): S23 (meeting abstract).*

Lee et al. (1991) The effects of the fluorinated pyrimidines FUR, FUdr, FUMP, and FdUMP on human Tenon's fibroblasts. Investigative Ophthalmology and Visual Science 32(9): 2599–2609.*

Nguyen et al. (1993) In vitro evaluation of antiproliferative potential of topical cyclo–oxygenase inhibitors in human Tenon's fibroblasts. Experimental Eye Research 57: 97–105.*

Rabowsky et al. (1996) The use of bioerodible polymers and daunorubicin in glaucoma filtration surgery. Ophthalmology 103: 800–807.*

Al–Aswad et al. (1996) Inhibition of fibroblast proliferation and enhancement of glaucoma filtration surgery in the rabbit with cytosine arabinoside. Investigative Ophthalmology and Visual Science 37(3): S23 (meeting abstract).*

Khaw et al. (1993) Effects of intraoperative 5–fluorouracil or mitomycin C on glaucoma fitration surgery in the rabbit. Opthalmology 100:367–372.*

Lee et al. (1991) The effects of the fluorinated pyrimidines FUR, FUdr, FUMP, and FdUMP on human Tenon's fibroblasts. Investigative Ophthalmology and Visual Science 32(9): 2599–2609.*

* cited by examiner

*Primary Examiner*—Anne-Marie Falk

(57) ABSTRACT

Methods and composition for the treatment of ocular disease with a cyclin dependent kinase inhibitor are provided.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 17 is confirmed.

Claim 16 is cancelled.

Claims 1, 7, 18 and 24 are determined to be patentable as amended.

Claims 2–6, 8–15, 19–23 and 25, dependent on an amended claim, are determined to be patentable.

1. A method for ameliorating glaucoma surgery failure in a mammal, the method comprising administering to an eye of said mammal during or after glaucoma surgery a nucleotide sequence encoding a p21 cyclin dependent kinase inhibitor, wherein the proliferation of ocular fibroblasts in said eye is inhibited so as to ameliorate said [glacoma] *glaucoma* surgery failure.

7. The method of claim 6, wherein the vector retains E4 [orf] *ORF* 6 and E4 [orf] *ORF* 6/7 but does not encode functional E4 peptide.

18. A method for ameliorating glaucoma surgery failure in a mammal, the method comprising administering to an eye of said mammal during or after glaucoma surgery a p21 cyclin dependent kinase inhibitor, wherein the proliferation of ocular fibroblasts in said eye is inhibited so as to ameliorate said [glacoma] *glaucoma* surgery failure.

24. The method of claim 23, wherein the adenoviral vector is TOCC [or XTCC].

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 447 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..447
      (D) OTHER INFORMATION: /product= "p16"
         /note= "p16 employed in construction of recombinant adenoviral vectors"

(xi) SEQUENCE DESCRIPTION: SEQ ID NO:1:

```
ATG GAG CCT TCG GCT GAC TGG CTG GCC ACG GCC GCG GCC CGG GGT CGG        48
Met Glu Pro Ser Ala Asp Trp Leu Ala Thr Ala Ala Ala Arg Gly Arg
 1               5                  10                  15

GTA GAG GAG GTG CGG GCG CTG CTG GAG GCG GGG GCG CTG CCC AAC GCA        96
Val Glu Glu Val Arg Ala Leu Leu Glu Ala Gly Ala Leu Pro Asn Ala
                20                  25                  30

CCG AAT AGT TAC GGT CGG AGG CCG ATC CAG GTC ATG ATG ATG GGC AGC       144
Pro Asn Ser Tyr Gly Arg Arg Pro Ile Gln Val Met Met Met Gly Ser
            35                  40                  45

GCC CGA GTG GCG GAG CTG CTG CTG CTC CAC GGC GCG GAG CCC AAC TGC       192
Ala Arg Val Ala Glu Leu Leu Leu Leu His Gly Ala Glu Pro Asn Cys
        50                  55                  60

GCC GAC CCC GCC ACT CTC ACC CGA CCC GTG CAC GAC GCT GCC CGG GAG       240
Ala Asp Pro Ala Thr Leu Thr Arg Pro Val His Asp Ala Ala Arg Glu
65                  70                  75                  80

GGC TTC CTG GAC ACG CTG GTG GTG CTG CAC CGG GCC GGG GCG CGG CTG       288
Gly Phe Leu Asp Thr Leu Val Val Leu His Arg Ala Gly Ala Arg Leu
                85                  90                  95

GAC GTG CGC GAT GCC TGG GGC CGT CTG CCC GTG GAC CTG GCT GAG GAG       336
Asp Val Arg Asp Ala Trp Gly Arg Leu Pro Val Asp Leu Ala Glu Glu
            100                 105                 110

CTG GGC CAT CGC GAT GTC GCA CGG TAC CTG CGC GCG GCT GCG GGG GGC       384
Leu Gly His Arg Asp Val Ala Arg Tyr Leu Arg Ala Ala Ala Gly Gly
        115                 120                 125

ACC AGA GGC AGT AAC CAT GCC CGC ATA GAT GCC GCG GAA GGT CCC TCA       432
```

```
Thr Arg Gly Ser Asn His Ala Arg Ile Asp Ala Ala Glu Gly Pro Ser
    130                 135                 140

GAC ATC CCC GAT TGA                                                         447
Asp Ile Pro Asp
145
```

(2) INFORMATION FOR SEQ ID NO:2:

(i) SEQUENCE CHARACTERISTICS:
        (A) LENGTH: 148 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Pro Ser Ala Asp Trp Leu Ala Thr Ala Ala Ala Arg Gly Arg
1               5                   10                  15

Val Glu Glu Val Arg Ala Leu Leu Glu Ala Gly Ala Leu Pro Asn Ala
                20                  25                  30

Pro Asn Ser Tyr Gly Arg Arg Pro Ile Gln Val Met Met Met Gly Ser
            35                  40                  45

Ala Arg Val Ala Glu Leu Leu Leu Leu His Gly Ala Glu Pro Asn Cys
        50                  55                  60

Ala Asp Pro Ala Thr Leu Thr Arg Pro Val His Asp Ala Ala Arg Glu
65                  70                  75                  80

Gly Phe Leu Asp Thr Leu Val Val Leu His Arg Ala Gly Ala Arg Leu
                85                  90                  95

Asp Val Arg Asp Ala Trp Gly Arg Leu Pro Val Asp Leu Ala Glu Glu
                100                 105                 110

Leu Gly His Arg Asp Val Ala Arg Tyr Leu Arg Ala Ala Ala Gly Gly
            115                 120                 125

Thr Arg Gly Ser Asn His Ala Arg Ile Asp Ala Ala Glu Gly Pro Ser
    130                 135                 140

Asp Ile Pro Asp
145
```

(2) INFORMATION FOR SEQ ID NO:3:

(i) SEQUENCE CHARACTERISTICS:
        (A) LENGTH: 156 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..156
        (D) OTHER INFORMATION: /note= "p16"

(xi) SEQUENCE DESCRIPTION: SEQ ID NO:3:

```
Met Glu Pro Ala Ala Gly Ser Ser Met Glu Pro Ser Ala Asp Trp Leu
1               5                   10                  15

Ala Thr Ala Ala Ala Arg Gly Arg Val Glu Glu Val Arg Ala Leu Leu
                20                  25                  30

Glu Ala Gly Ala Leu Pro Asn Ala Pro Asn Ser Tyr Gly Arg Arg Pro
            35                  40                  45

Ile Gln Val Met Met Met Gly Ser Ala Arg Val Ala Glu Leu Leu Leu
        50                  55                  60
```

```
Leu His Gly Ala Glu Pro Asn Cys Ala Asp Pro Ala Thr Leu Thr Arg
 65              70                  75                  80

Pro Val His Asp Ala Ala Arg Glu Gly Phe Leu Asp Thr Leu Val Val
                 85                  90                  95

Leu His Arg Ala Gly Ala Arg Leu Asp Val Arg Asp Ala Trp Gly Arg
                100                 105                 110

Leu Pro Val Asp Leu Ala Glu Glu Leu Gly His Arg Asp Val Ala Arg
            115                 120                 125

Tyr Leu Arg Ala Ala Gly Gly Thr Arg Gly Ser Asn His Ala Arg
130                 135                 140

Ile Asp Ala Ala Glu Gly Pro Ser Asp Ile Pro Asp
145                 150                 155
```

(2) INFORMATION FOR SEQ ID NO:4:

(i) SEQUENCE CHARACTERISTICS:
        (A) LENGTH: 495 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..495
        (D) OTHER INFORMATION: /product= "p21"
            /note= "p21 employed in construction of recombinant
            adenoviral vectors"

(xi) SEQUENCE DESCRIPTION: SEQ ID NO:4:

```
ATG TCA GAA CCG GCT GGG GAT GTC CGT CAG AAC CCA TGC GGC AGC AAG        48
Met Ser Glu Pro Ala Gly Asp Val Arg Gln Asn Pro Cys Gly Ser Lys
 1               5                  10                  15

GCC TGC CGC CGC CTC TTC GGC CCA GTG GAC AGC GAG CAG CTG AGC CGC        96
Ala Cys Arg Arg Leu Phe Gly Pro Val Asp Ser Glu Gln Leu Ser Arg
                20                  25                  30

GAC TGT GAT GCG CTA ATG GCG GGC TGC ATC CAG GAG GCC CGT GAG CGA       144
Asp Cys Asp Ala Leu Met Ala Gly Cys Ile Gln Glu Ala Arg Glu Arg
             35                  40                  45

TGG AAC TTC GAC TTT GTC ACC GAG ACA CCA CTG GAG GGT GAC TTC GCC       192
Trp Asn Phe Asp Phe Val Thr Glu Thr Pro Leu Glu Gly Asp Phe Ala
 50                  55                  60

TGG GAG CGT GTG CGG GGC CTT GGC CTG CCC AAG CTC TAC CTT CCC ACG       240
Trp Glu Arg Val Arg Gly Leu Gly Leu Pro Lys Leu Tyr Leu Pro Thr
 65                  70                  75                  80

GGG CCC CGG CGA GGC CGG GAT GAG TTG GGA GGA GGC AGG CGG CCT GGC       288
Gly Pro Arg Arg Gly Arg Asp Glu Leu Gly Gly Gly Arg Arg Pro Gly
                 85                  90                  95

ACC TCA CCT GCT CTG CTG CAG GGG ACA GCA GAG GAA GAC CAT GTG GAC       336
Thr Ser Pro Ala Leu Leu Gln Gly Thr Ala Glu Glu Asp His Val Asp
                100                 105                 110

CTG TCA CTG TCT TGT ACC CTT GTG CCT CGC TCA GGG GAG CAG GCT GAA       384
Leu Ser Leu Ser Cys Thr Leu Val Pro Arg Ser Gly Glu Gln Ala Glu
            115                 120                 125

GGG TCC CCA GGT GGA CCT GGA GAC TCT CAG GGT CGA AAA CGG CGG CAG       432
Gly Ser Pro Gly Gly Pro Gly Asp Ser Gln Gly Arg Lys Arg Arg Gln
130                 135                 140

ACC AGC ATG ACA GAT TTC TAC CAC TCC AAA CGC CGG CTG ATC TTC TCC       480
Thr Ser Met Thr Asp Phe Tyr His Ser Lys Arg Arg Leu Ile Phe Ser
145                 150                 155                 160

AAG AGG AAG CCC TAA                                                   495
```

```
Lys Arg Lys Pro (2) INFORMATION FOR SEQ ID NO:5:

(i) SEQUENCE CHARACTERISTICS:
        (A) LENGTH: 164 amino acids
        (B) TYPE: amino acid
        (D) TOPOLOGY: linear (ii) MOLECULE TYPE: protein (xi) SEQUENCE DESCRIPTION: SEQ ID NO:5:

Met Ser Glu Pro Ala Gly Asp Val Arg Gln Asn Pro Cys Gly Ser Lys
 1               5                  10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
        35                  40                  45

Trp Asn Phe Asp Phe Val Thr Glu Thr Pro Leu Glu Gly Asp Phe Ala
 50                  55                  60

Trp Glu Arg Val Arg Gly Leu Gly Leu Pro Lys Leu Tyr Leu Pro Thr
65                  70                  75                  80

Gly Pro Arg Arg Gly Arg Asp Glu Leu Gly Gly Gly Arg Arg Pro Gly
                85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Arg Gln
130                 135                 140

Thr Ser Met Thr Asp Phe Tyr His Ser Lys Arg Arg Leu Ile Phe Ser
145                 150                 155                 160

Lys Arg Lys Pro (2) INFORMATION FOR SEQ ID NO:6:

(i) SEQUENCE CHARACTERISTICS:
        (A) LENGTH: 1653 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1653
        (D) OTHER INFORMATION: /product= "p56-Rb"
            /note= "p56-Rb employed in construction of recombinant
            adenoviral vectors"

(xi) SEQUENCE DESCRIPTION: SEQ ID NO:6:

ATG AAC ACT ATC CAA CAA TTA ATG ATG ATT TTA AAT TCT GCA AGT GAT       48
Met Asn Thr Ile Gln Gln Leu Met Met Ile Leu Asn Ser Ala Ser Asp
 1               5                  10                  15

CAA CCT TCA GAA AAT CTG ATT TCC TAT TTT AAC AAC TGC ACA GTG AAT       96
Gln Pro Ser Glu Asn Leu Ile Ser Tyr Phe Asn Asn Cys Thr Val Asn
            20                  25                  30

CCA AAA GAA AGT ATA CTG AAA AGA GTG AAG GAT ATA GGA TAC ATC TTT      144
Pro Lys Glu Ser Ile Leu Lys Arg Val Lys Asp Ile Gly Tyr Ile Phe
        35                  40                  45

AAA GAG AAA TTT GCT AAA GCT GTG GGA CAG GGT TGT GTC GAA ATT GGA      192
```

```
                                                      -continued

Lys Glu Lys Phe Ala Lys Ala Val Gly Gln Gly Cys Val Glu Ile Gly
     50                  55                  60

TCA CAG CGA TAC AAA CTT GGA GTT CGC TTG TAT TAC CGA GTA ATG GAA        240
Ser Gln Arg Tyr Lys Leu Gly Val Arg Leu Tyr Tyr Arg Val Met Glu
 65                  70                  75                  80

TCC ATG CTT AAA TCA GAA GAA GAA CGA TTA TCC ATT CAA AAT TTT AGC        288
Ser Met Leu Lys Ser Glu Glu Glu Arg Leu Ser Ile Gln Asn Phe Ser
                 85                  90                  95

AAA CTT CTG AAT GAC AAC ATT TTT CAT ATG TCT TTA TTG GCG TGC GCT        336
Lys Leu Leu Asn Asp Asn Ile Phe His Met Ser Leu Leu Ala Cys Ala
             100                 105                 110

CTT GAG GTT GTA ATG GCC ACA TAT AGC AGA AGT ACA TCT CAG AAT CTT        384
Leu Glu Val Val Met Ala Thr Tyr Ser Arg Ser Thr Ser Gln Asn Leu
         115                 120                 125

GAT TCT GGA ACA GAT TTG TCT TTC CCA TGG ATT CTG AAT GTG CTT AAT        432
Asp Ser Gly Thr Asp Leu Ser Phe Pro Trp Ile Leu Asn Val Leu Asn
 130                 135                 140

TTA AAA GCC TTT GAT TTT TAC AAA GTG ATC GAA AGT TTT ATC AAA GCA        480
Leu Lys Ala Phe Asp Phe Tyr Lys Val Ile Glu Ser Phe Ile Lys Ala
145                 150                 155                 160

GAA GGC AAC TTG ACA AGA GAA ATG ATA AAA CAT TTA GAA CGA TGT GAA        528
Glu Gly Asn Leu Thr Arg Glu Met Ile Lys His Leu Glu Arg Cys Glu
                 165                 170                 175

CAT CGA ATC ATG GAA TCC CTT GCA TGG CTC TCA GAT TCA CCT TTA TTT        576
His Arg Ile Met Glu Ser Leu Ala Trp Leu Ser Asp Ser Pro Leu Phe
             180                 185                 190

GAT CTT ATT AAA CAA TCA AAG GAC CGA GAA GGA CCA ACT GAT CAC CTT        624
Asp Leu Ile Lys Gln Ser Lys Asp Arg Glu Gly Pro Thr Asp His Leu
         195                 200                 205

GAA TCT GCT TGT CCT CTT AAT CTT CCT CTC CAG AAT AAT CAC ACT GCA        672
Glu Ser Ala Cys Pro Leu Asn Leu Pro Leu Gln Asn Asn His Thr Ala
 210                 215                 220

GCA GAT ATG TAT CTT TCT CCT GTA AGA TCT CCA AAG AAA AAA GGT TCA        720
Ala Asp Met Tyr Leu Ser Pro Val Arg Ser Pro Lys Lys Lys Gly Ser
225                 230                 235                 240

ACT ACG CGT GTA AAT TCT ACT GCA AAT GCA GAG ACA CAA GCA ACC TCA        768
Thr Thr Arg Val Asn Ser Thr Ala Asn Ala Glu Thr Gln Ala Thr Ser
                 245                 250                 255

GCC TTC CAG ACC CAG AAG CCA TTG AAA TCT ACC TCT CTT TCA CTG TTT        816
Ala Phe Gln Thr Gln Lys Pro Leu Lys Ser Thr Ser Leu Ser Leu Phe
             260                 265                 270

TAT AAA AAA GTG TAT CGG CTA GCC TAT CTC CGG CTA AAT ACA CTT TGT        864
Tyr Lys Lys Val Tyr Arg Leu Ala Tyr Leu Arg Leu Asn Thr Leu Cys
         275                 280                 285

GAA CGC CTT CTG TCT GAG CAC CCA GAA TTA GAA CAT ATC ATC TGG ACC        912
Glu Arg Leu Leu Ser Glu His Pro Glu Leu Glu His Ile Ile Trp Thr
 290                 295                 300

CTT TTC CAG CAC ACC CTG CAG AAT GAG TAT GAA CTC ATG AGA GAC AGG        960
Leu Phe Gln His Thr Leu Gln Asn Glu Tyr Glu Leu Met Arg Asp Arg
305                 310                 315                 320

CAT TTG GAC CAA ATT ATG ATG TGT TCC ATG TAT GGC ATA TGC AAA GTG       1008
His Leu Asp Gln Ile Met Met Cys Ser Met Tyr Gly Ile Cys Lys Val
                 325                 330                 335

AAG AAT ATA GAC CTT AAA TTC AAA ATC ATT GTA ACA GCA TAC AAG GAT       1056
Lys Asn Ile Asp Leu Lys Phe Lys Ile Ile Val Thr Ala Tyr Lys Asp
             340                 345                 350

CTT CCT CAT GCT GTT CAG GAG ACA TTC AAA CGT GTT TTG ATC AAA GAA       1104
Leu Pro His Ala Val Gln Glu Thr Phe Lys Arg Val Leu Ile Lys Glu
         355                 360                 365
```

```
GAG GAG TAT GAT TCT ATT ATA GTA TTC TAT AAC TCG GTC TTC ATG CAG    1152
Glu Glu Tyr Asp Ser Ile Ile Val Phe Tyr Asn Ser Val Phe Met Gln
    370             375                 380

AGA CTG AAA ACA AAT ATT TTG CAG TAT GCT TCC ACC AGG CCC CCT ACC    1200
Arg Leu Lys Thr Asn Ile Leu Gln Tyr Ala Ser Thr Arg Pro Pro Thr
385             390                 395                 400

TTG TCA CCA ATA CCT CAC ATT CCT CGA AGC CCT TAC AAG TTT CCT AGT    1248
Leu Ser Pro Ile Pro His Ile Pro Arg Ser Pro Tyr Lys Phe Pro Ser
                405                 410                 415

TCA CCC TTA CGG ATT CCT GGA GGG AAC ATC TAT ATT TCA CCC CTG AAG    1296
Ser Pro Leu Arg Ile Pro Gly Gly Asn Ile Tyr Ile Ser Pro Leu Lys
            420                 425                 430

AGT CCA TAT AAA ATT TCA GAA GGT CTG CCA ACA CCA ACA AAA ATG ACT    1344
Ser Pro Tyr Lys Ile Ser Glu Gly Leu Pro Thr Pro Thr Lys Met Thr
            435                 440                 445

CCA AGA TCA AGA ATC TTA GTA TCA ATT GGT GAA TCA TTC GGG ACT TCT    1392
Pro Arg Ser Arg Ile Leu Val Ser Ile Gly Glu Ser Phe Gly Thr Ser
450                 455                 460

GAG AAG TTC CAG AAA ATA AAT CAG ATG GTA TGT AAC AGC GAC CGT GTG    1440
Glu Lys Phe Gln Lys Ile Asn Gln Met Val Cys Asn Ser Asp Arg Val
465                 470                 475                 480

CTC AAA AGA AGT GCT GAA GGA AGC AAC CCT CCT AAA CCA CTG AAA AAA    1488
Leu Lys Arg Ser Ala Glu Gly Ser Asn Pro Pro Lys Pro Leu Lys Lys
                485                 490                 495

CTA CGC TTT GAT ATT GAA GGA TCA GAT GAA GCA GAT GGA AGT AAA CAT    1536
Leu Arg Phe Asp Ile Glu Gly Ser Asp Glu Ala Asp Gly Ser Lys His
            500                 505                 510

CTC CCA GGA GAG TCC AAA TTT CAG CAG AAA CTG GCA GAA ATG ACT TCT    1584
Leu Pro Gly Glu Ser Lys Phe Gln Gln Lys Leu Ala Glu Met Thr Ser
            515                 520                 525

ACT CGA ACA CGA ATG CAA AAG CAG AAA ATG AAT GAT AGC ATG GAT ACC    1632
Thr Arg Thr Arg Met Gln Lys Gln Lys Met Asn Asp Ser Met Asp Thr
530                 535                 540

TCA AAC AAG GAA GAG AAA TGA                                        1653
Ser Asn Lys Glu Glu Lys
545                 550

(2) INFORMATION FOR SEQ ID NO:7:

(i) SEQUENCE CHARACTERISTICS:
        (A) LENGTH: 550 amino acids
        (B) TYPE: amino acid
        (D) TOPOLOGY: linear (ii) MOLECULE TYPE: protein (xi) SEQUENCE DESCRIPTION: SEQ ID NO:7:

Met Asn Thr Ile Gln Gln Leu Met Met Ile Leu Asn Ser Ala Ser Asp
1               5                   10                  15

Gln Pro Ser Glu Asn Leu Ile Ser Tyr Phe Asn Asn Cys Thr Val Asn
            20                  25                  30

Pro Lys Glu Ser Ile Leu Lys Arg Val Lys Asp Ile Gly Tyr Ile Phe
        35                  40                  45

Lys Glu Lys Phe Ala Lys Ala Val Gly Gln Gly Cys Val Glu Ile Gly
    50                  55                  60

Ser Gln Arg Tyr Lys Leu Gly Val Arg Leu Tyr Tyr Arg Val Met Glu
65                  70                  75                  80

Ser Met Leu Lys Ser Glu Glu Glu Arg Leu Ser Ile Gln Asn Phe Ser
                85                  90                  95

Lys Leu Leu Asn Asp Asn Ile Phe His Met Ser Leu Leu Ala Cys Ala
```

-continued

```
                100             105             110
Leu Glu Val Val Met Ala Thr Tyr Ser Arg Ser Thr Ser Gln Asn Leu
            115                 120             125

Asp Ser Gly Thr Asp Leu Ser Phe Pro Trp Ile Leu Asn Val Leu Asn
        130                 135             140

Leu Lys Ala Phe Asp Phe Tyr Lys Val Ile Glu Ser Phe Ile Lys Ala
145             150             155                         160

Glu Gly Asn Leu Thr Arg Glu Met Ile Lys His Leu Glu Arg Cys Glu
                165             170              175

His Arg Ile Met Glu Ser Leu Ala Trp Leu Ser Asp Ser Pro Leu Phe
            180             185                 190

Asp Leu Ile Lys Gln Ser Lys Asp Arg Glu Gly Pro Thr Asp His Leu
        195                 200             205

Glu Ser Ala Cys Pro Leu Asn Leu Pro Leu Gln Asn Asn His Thr Ala
    210             215              220

Ala Asp Met Tyr Leu Ser Pro Val Arg Ser Pro Lys Lys Lys Gly Ser
225             230              235             240

Thr Thr Arg Val Asn Ser Thr Ala Asn Ala Glu Thr Gln Ala Thr Ser
                245             250              255

Ala Phe Gln Thr Gln Lys Pro Leu Lys Ser Thr Ser Leu Ser Leu Phe
            260             265              270

Tyr Lys Lys Val Tyr Arg Leu Ala Tyr Leu Arg Leu Asn Thr Leu Cys
        275             280              285

Glu Arg Leu Leu Ser Glu His Pro Glu Leu Glu His Ile Ile Trp Thr
    290             295              300

Leu Phe Gln His Thr Leu Gln Asn Glu Tyr Glu Leu Met Arg Asp Arg
305             310             315                         320

His Leu Asp Gln Ile Met Met Cys Ser Met Tyr Gly Ile Cys Lys Val
                325             330              335

Lys Asn Ile Asp Leu Lys Phe Lys Ile Ile Val Thr Ala Tyr Lys Asp
            340             345              350

Leu Pro His Ala Val Gln Glu Thr Phe Lys Arg Val Leu Ile Lys Glu
        355             360              365

Glu Glu Tyr Asp Ser Ile Ile Val Phe Tyr Asn Ser Val Phe Met Gln
    370             375              380

Arg Leu Lys Thr Asn Ile Leu Gln Tyr Ala Ser Thr Arg Pro Pro Thr
385             390             395                         400

Leu Ser Pro Ile Pro His Ile Pro Arg Ser Pro Tyr Lys Phe Pro Ser
                405             410              415

Ser Pro Leu Arg Ile Pro Gly Gly Asn Ile Tyr Ile Ser Pro Leu Lys
            420             425              430

Ser Pro Tyr Lys Ile Ser Glu Gly Leu Pro Thr Pro Thr Lys Met Thr
        435             440              445

Pro Arg Ser Arg Ile Leu Val Ser Ile Gly Glu Ser Phe Gly Thr Ser
    450             455              460

Glu Lys Phe Gln Lys Ile Asn Gln Met Val Cys Asn Ser Asp Arg Val
465             470             475                         480

Leu Lys Arg Ser Ala Glu Gly Ser Asn Pro Pro Lys Pro Leu Lys Lys
                485             490              495

Leu Arg Phe Asp Ile Glu Gly Ser Asp Glu Ala Asp Gly Ser Lys His
            500             505              510

Leu Pro Gly Glu Ser Lys Phe Gln Gln Lys Leu Ala Glu Met Thr Ser
        515             520              525
```

-continued

```
Thr Arg Thr Arg Met Gln Lys Gln Lys Met Asn Asp Ser Met Asp Thr
    530                 535                 540

Ser Asn Lys Glu Glu Lys
545                 550
```